United States Patent [19]

Kleemann et al.

[11] Patent Number: 5,698,581

[45] Date of Patent: Dec. 16, 1997

[54] SUBSTITUTED N-HETEROAROYLGUANIDINES, A PROCESS FOR THEIR PREPARATION, THEIR USE AS A MEDICAMENT OR DIAGNOSTIC AGENT, AND A MEDICAMENT CONTAINING THEM

[75] Inventors: Heinz-Werner Kleemann, Bischofsheim; Hans-Jochen Lang, Hofheim; Jan-Robert Schwark, Frankfurt; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 418,434

[22] Filed: Apr. 7, 1995

[30] Foreign Application Priority Data

Apr. 11, 1994 [DE] Germany .................. 44 12 334.5

[51] Int. Cl.⁶ .................... A61K 31/38; C07D 333/22
[52] U.S. Cl. .................... 514/447; 514/312; 514/313; 514/314; 514/307; 514/309; 514/310; 514/326; 514/397; 514/422; 514/444; 514/445; 514/448; 546/153; 546/155; 546/157; 546/159; 546/162; 546/163; 546/167; 546/141; 546/142; 546/143; 546/144; 546/284.7; 546/212; 546/213; 548/315.1; 548/527; 549/59; 549/60; 549/61; 549/62; 549/63; 549/64; 549/69; 549/70
[58] Field of Search .................... 546/153, 155, 546/157, 159, 162, 163, 167, 141, 142, 143, 144, 284, 212, 213, 284.7; 548/315.1, 527, 212, 213, 215.1; 549/59, 60, 61, 62, 63, 64, 69, 70; 514/312, 313, 314, 307, 309, 310, 326, 397, 422, 444, 445, 448, 447

[56] References Cited

U.S. PATENT DOCUMENTS

| | | |
|---|---|---|
| 3,622,595 | 11/1971 | Marchetti . |
| 3,752,819 | 8/1973 | Philippe . |
| 4,894,376 | 1/1990 | Morad et al. .................... 514/255 |
| 5,002,965 | 3/1991 | Ramwell et al. .................... 514/468 |
| 5,091,394 | 2/1992 | Englert et al. .................... 514/331 |
| 5,260,091 | 11/1993 | Locke et al. .................... 426/649 |
| 5,292,755 | 3/1994 | Englert et al. .................... 514/331 |
| 5,364,868 | 11/1994 | Englert et al. .................... 514/331 |
| 5,373,024 | 12/1994 | Lang et al. .................... 514/618 |
| 5,416,094 | 5/1995 | Lal et al. .................... 514/307 |
| 5,516,805 | 5/1996 | Lang et al. .................... 514/620 |
| 5,547,953 | 8/1996 | Weichert et al. .................... 514/226.5 |
| 5,559,153 | 9/1996 | Schwark et al. .................... 514/597 |
| 5,567,734 | 10/1996 | Schwark et al. .................... 514/617 |
| 5,571,842 | 11/1996 | Kleemann et al. .................... 514/618 |
| 5,591,754 | 1/1997 | Lang et al. .................... 514/331 |
| 5,631,293 | 5/1997 | Kleemann et al. .................... 514/563 |

FOREIGN PATENT DOCUMENTS

| | | |
|---|---|---|
| 973883 | 9/1975 | Canada . |
| 0622356 | 11/1994 | European Pat. Off. . |

OTHER PUBLICATIONS

Skvortsov et al., "Furyol–or tetrahydrofuroylguanidines," Chemical Abstracts, 79(9):352, Abstract No. 53170t (1973).

Stolyarchuk et al., "Synthesis of Furoylguanidines and Comparison of their Pharmacological Properties with the Properties of Furoylureas," Chemical Abstracts, 86(17):522, Abstract No. 121071h (1977).

Aleksashin et al., "Spectral Characteristics of Ureides, Thioureides, Isoselenoureides, and Guanidines," Chemical Abstracts 101(9):593, Abstract No. 72124v (1984).

Escobales et al, "Na+/Na+ Exhange and Na+/H+ Antiport in Rabbit Erythrocytes: Two Distinct Transport Systems," J. Membrane Biol., 120:41–49 (1991).

Schmid et al., "Na+/H+ Exchange in Porcine Cerebral Capillary Endothelial Cells is Inhibited by a Benzoylguanidine Derivative", Biochemical and Biophysical Research Communications, 184(1):112–117 (1992).

Düsing et al., "Zur Klinischen Bedeutung des Na+/H+–Antiports," Medizinische Klinik, 87(7):378–384 (1992), no translation available.

Fujimoto, "Isoxazolylcarbonylureas", Chemical Abstracts, 72(13):401, Abstract No. 66928b (1970).

Derwent Abstract of DE 2055727.
Derwent Abstract of EP 416499.
Derwent Abstract of WO 9304048.
Derwent Abstract of EP 556672.
Derwent Abstract of EP 556673.
Derwent Abstract of EP 556674.
Derwent Abstract of EP 589336.
Derwent Abstract of EP 590455.
Derwent Abstract of EP 639573.
Derwent Abstract of EP 577024.

Primary Examiner—C. Warren Ivy
Assistant Examiner—Garth M. Dahlen
Attorney, Agent, or Firm—Finnegan, Henderson, Farabow, Garrett & Dunner, L.L.P.

[57] ABSTRACT

The invention relates to heteroaroylguanidines of the formula I

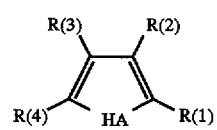

in which the substituents HA and R(1) to R(5) have the meanings given in the specification. These compounds exhibit very good antiarrhythmic properties and are outstandingly suitable for use as antiarrhythmic pharmaceuticals possessing a cardioprotective component for the prophylaxis and treatment of infarction and for the treatment of angina pectoris, in connection with which they also inhibit or strongly reduce, in a preventative manner, the pathophysiological processes associated with the genesis of ischemically induced damage, in particular associated with the elicitation of ischemically induced cardiac arrhythmias.

17 Claims, No Drawings

SUBSTITUTED N-HETEROAROYLGUANIDINES, A PROCESS FOR THEIR PREPARATION, THEIR USE AS A MEDICAMENT OR DIAGNOSTIC AGENT, AND A MEDICAMENT CONTAINING THEM

The invention relates to heteroaroylguanidines of the formula I

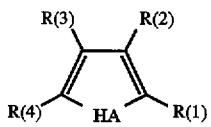

in which:

HA is $SO_m$, O, or NR(5), m is zero, 1 or 2,

R(5) is hydrogen, $(C_1-C_8)$-alkyl or $-C_{am}H_{2am}R(81)$, am is zero, 1 or 2

R(81) is $(C_3-C_8)$-cycloalkyl, or phenyl which is not substituted or is substituted by 1–3 substituents from the group F, Cl, $CF_3$, methyl, methoxy or NR(82)R(83), with R(82) and R(83) being H or $CH_3$;

or

R(81) is $(C_1-C_9)$-heteroaryl which is linked via C or N and which is unsubstituted or is substituted by 1–3 substituents from the group F, Cl, $CF_3$, $CH_3$, methoxy, hydroxyl, amino, methylamino, or dimethylamino;

one of the two substituents R(1) and R(2) is $-CO-N=C(NH_2)_2$, and whichever is the other is hydrogen, F, Cl, Br, I, $(C_1-C_3)$-alkyl, $-OR(6)$, $C_rF_{2r+1}$, $-CO-N=C(NH_2)_2$ or $-NR(6)R(7)$, R(6) and R(7) are, independently, hydrogen or $(C_1-C_3)$-alkyl, r is 1, 2, 3 or 4, R(3) and R(4) are, independently of each other, hydrogen, F, Cl, Br, I, $-C\equiv N$, $X-(CH_2)_p-(C_q-F_{2q+1})$, R(8) $-SO_{bm}$, R(9)R(10)N$-$CO, R(11)$-$CO$-$ or R(12)R(13)N$-$SO$_2-$, where the perfluoroalkyl group is straight-chain or branched, X is oxygen, S or NR(14), R(14) is H or $(C_1-C_3)$-alkyl, bm is zero, 1 or 2, p is zero, 1 or 2, q is zero, 1, 2, 3, 4, 5 or 6, R(8), R(9), R(11) and R(12) are, independently, $(C_1-C_8)$-alkyl, $(C_3-C_6)$-alkenyl, $-C_nH_{2n}-R(15)$ or $CF_3$, n is zero, 1, 2, 3 or 4, R(15) is $(C_3-C_7)$-cycloalkyl, or phenyl which is not substituted or is substituted by 1–3 substituents from the group F, Cl, $CF_3$, methyl, methoxy or NR(16)R(17) with R(16) and R(17) being H or $C_1-C_4$-alkyl, where R(9), R(11) and R(12) also have the meaning of H, R(10) and R(13) are, independently, H or $(C_1-C_4)$-alkyl, where R(9) and R(10) and also R(12) and R(13) can together be 4 or 5 methylene groups, of which one $CH_2$ group can be replaced by oxygen, S, NH, N$-CH_3$ or N-benzyl, or R(3) and R(4) are, independently of each other, $(C_1-C_8)$-alkyl or $-C_{al}H_{2al}R(18)$, al is zero, 1 or 2, R(18) is $(C_3-C_8)$-cycloalkyl, or phenyl which is not substituted or is substituted by 1–3 substituents from the group F, Cl, $CF_3$, methyl, methoxy or NR(19)R(20), with R(19) and R(20) being H or R(3) and R(4) are, independently of each other, $(C_1-C_9)$-heteroaryl, which is linked via C or N and which is unsubstituted or is substituted by 1–3 substituents from the group F, Cl, $CF_3$, $CH_3$, methoxy, hydroxyl, amino, methylamino or dimethylamino;

or

R(3) and R(4) are, independently of each other,

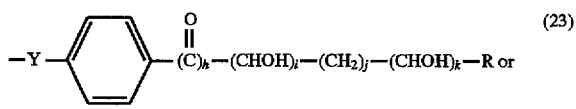

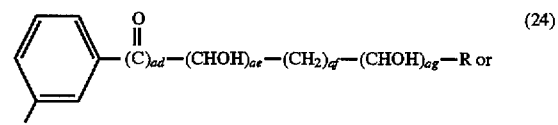

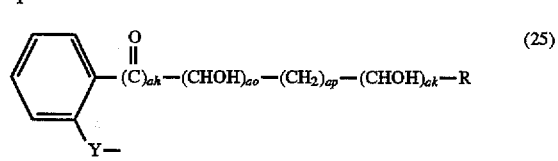

Y is oxygen, $-S-$ or $-NR(22)-$, h, ad and ah are, independently, zero or 1, i, j, k, ae, af, ag, ao, ap and ak are, independently, zero, 1, 2, 3 or 4, where, however, in each case, h, i and k are not simultaneously zero, ad, ae and ag are not simultaneously zero, and ah, ao and ak are not simultaneously zero, R(23), R(24), R(25) and R(22) are, independently, hydrogen or $(C_1-C_3)$-alkyl, or R(3) and R(4) are, independently of each other, hydrogen, F, Cl, Br, I, CN, $(C_1-C_8)$-alkyl, $(C_1-C_8)$-perfluoroalkyl, $(C_3-C_8)$-alkenyl or $-C_gH_{2g}R(26)$, g is zero, 1, 2, 3 or 4, R(26) is $(C_3-C_8)$-cycloalkyl, phenyl, biphenylyl or naphthyl, where the aromatic radicals are not substituted or are substituted by 1–3 substituents from the group F, Cl, $CF_3$, methyl, methoxy or NR (27) R (28), with R(27) and R(28) being H, $(C_1-C_4)$-alkyl or $(C_1-C_4)$-perfluoroalkyl;

or

R(3) and R(4) are, independently of each other, SR(29), $-OR(30)$, $-NR(31)R(32)$ or $-CR(33)R(34)R(35)$;

R(29), R(30), R(31) and R(33) are, independently, $-C_aH_{2a}-(C_1-C_9)$-heteroaryl which is unsubstituted or is substituted by 1–3 substituents from the group F, Cl, $CF_3$, $CH_3$, methoxy, hydroxyl, amino, methylamino or dimethylamino, a is zero, 1 or 2, R(32), R(34) and R(35) are, independently of each other, defined as R (29), or are hydrogen, $(C_1-C_4)$-alkyl or $(C_1-C_4)$-perfluoroalkyl;

or

R(3) and R(4) are, independently of each other,

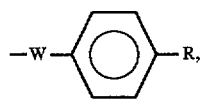 (96)

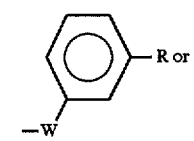 (97)

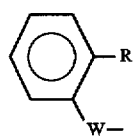 (98)

R(96), R(97) and R(98) are, independently, $(C_1-C_9)$-heteroaryl,
which is linked via C or N and which is unsubstituted or is substituted by 1–3 substituents from the group F, Cl, $CF_3$, $CH_3$, methoxy, hydroxyl, amino, methylamino, dimethylamino or benzyl,
W is oxygen, S or NR(36)—, R(36) is H or $(C_1-C_4)$-alkyl, or
R(3) and R(4) are, independently of each other,
R(37)—$SO_{cm}$ or R(38)R(39)N—$SO_2$—,
cm is 1 or 2,
R(37) is $(C_1-C_8)$-alkyl, $(C_1-C_8)$-perfluoroalkyl, $(C_3-C_8)$-alkenyl or —$C_sH_{2s}$—R(40),
s is zero, 1, 2, 3 or 4,
R(40) is $(C_3-C_8)$-cycloalkyl, phenyl, biphenylyl or naphthyl,
where the aromatic radicals are not substituted or are substituted by 1–3 substituents from the group F, Cl, $CF_3$, methyl, methoxy or NR(41)R(42), with R(41) and R(42) being H, $(C_1-C_4)$-alkyl or $(C_1-C_4)$-perfluoroalkyl;
R(38) is H, $(C_1-C_8)$-alkyl, $(C_1-C_8)$-perfluoroalkyl, $(C_3-C_8)$-alkenyl or —$C_wH_{2w}$—R(43),
w is zero, 1, 2, 3 or 4,
R(43) is $(C_3-C_8)$-cycloalkyl, phenyl, biphenylyl or naphthyl where the aromatic radicals are not substituted or are substituted by 1–3 substituents from the group F, Cl, $CF_3$, methyl, methoxy or NR(44) R(45), with R(44) and R(45) being H, $(C_1-C_4)$-alkyl or $(C_1-C_4)$-perfluoroalkyl,
R(39) is H, $(C_1-C_4)$-alkyl or $(C_1-C_4)$-perfluoroalkyl,
where R(38) and R(39) can together be 4 or 5 methylene groups, of which one $CH_2$ group can be replaced by oxygen, S, NH, N—$CH_3$ or N-benzyl;

or
R(3) and R(4) are, independently of each other, R(46) X(1)—,
X(1) is oxygen, S, NR(47), (D=O)A— or NR(48) C=MN(*)R(49)—,
M is oxygen or S,
A is oxygen or NR(50),
D is C or SO,
R(46) is $(C_1-C_8)$-alkyl, $(C_3-C_8)$-alkenyl, $(CH_2)_bC_dF_{2d+1}$ or —$C_xH_{2x}$—R(51),
b is zero or 1,
d is 1, 2, 3, 4, 5, 6 or 7,
x is zero, 1, 2, 3 or 4,
R(51) is $(C_3-C_8)$-cycloalkyl, phenyl, biphenylyl, naphthyl, where the aromatic radicals are not substituted or are substituted by 1–3 substituents from the group F, Cl, $CF_3$, methyl, methoxy or NR(52) R(53); with R(52) and R(53) being H, $(C_1-C_4)$-alkyl or $(C_1-C_4)$-perfluoroalkyl;
R(47), R(48) and R(50) are, independently, hydrogen, $(C_1-C_4)$-alkyl or $(C_1-C_4)$-perfluoroalkyl,
R(49) is defined as R(46), where
R(46) and R(47) and, respectively, R(46) and R(48) can together be 4 or 5 methylene groups, of which one $CH_2$ group can be replaced by oxygen, S, NH, N—$CH_3$ or N-benzyl,
where A and $N^{(*)}$ are bonded to the phenyl nucleus of the benzoylguanidine parent substance;

or
R(3) and R(4) are, independently of each other, —SR(64), —OR(65), —NHR(66), —NR(67)R(68), —CHR(69) R(70),

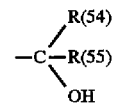

$-C\equiv CR(56)$, $-\overset{R(58)}{\underset{|}{C}}-C-R(57)$,

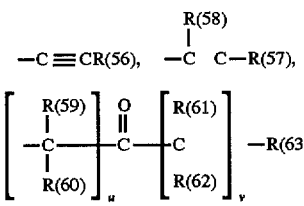

R(64), R(65), R(66), R(67) and R(69) are, identically or differently,
—$(CH_2)_y$—$(CHOH)_z$—$(CH_2)_{aa}$—$(CH_2OH)_t$—R(71) or —$(CH_2)_{ab}$—O—$(CH_2—CH_2O)_{ac}$—R(72),
R(71) and R(72) are hydrogen or methyl,
u is 1, 2, 3 or 4,
v is zero, 1, 2, 3 or 4, y, z and aa are, identically or differently, zero, 1, 2, 3 or 4,
t is 1, 2, 3 or 4,
R(68), R(70), R(54) and R(55) are, identically or differently,
hydrogen or $(C_1-C_6)$-alkyl, or
R(69) and R(70) and, respectively, R(54) and R(55) are, together with the carbon atom carrying them, a $(C_3-C_8)$-cycloalkyl;
R(63) is
H, $(C_1-C_6)$-alkyl, $(C_3-C_8)$-cycloalkyl or —$C_eH_{2e}$—R(73),
e is zero, 1, 2, 3 or 4,
R(56), R(57) and R(73) are, independently, phenyl,
which is unsubstituted or is substituted by 1–3 substituents from the group F, Cl, $CF_3$, methyl, methoxy or NR(74)R(75) with R(74) and R(75) being H or $(C_1-C_4)$-alkyl,
or R(56), R(57) and R(73) are, independently, $(C_1-C_9)$-heteroaryl,
which is unsubstituted or is substituted as phenyl;
R(58), R(59), R(60), R(61) and R(62) are hydrogen or methyl, or
R(3) and R(4) are, independently of each other, R(76) —NH—$SO_2$—,
R(76) is R(77)R(78)N—(C=Y')—, Y' is oxygen, S or N—R(79),
R(77) and R(78) are, identically or differently, H, (C₁-C₈)-alkyl, (C₃-C₆)-alkenyl, or $C_fH_{2f}$—R(80),
f is zero, 1, 2, 3 or 4,
R(80) is (C₅-C₇)-cycloalkyl, or phenyl
which is unsubstituted or is substituted by 1-3 substituents from the group F, Cl, CF₃, methoxy or (C₁-C₄)-alkyl, or
R(77) and R(78) together form 4 or 5 methylene groups, of which one CH₂ group can be replaced by oxygen, S, NH, N—CH₃ or N-benzyl, where
R(79) is defined as R(77) or is amidine;

or

R(3) and R(4) are, independently of each other, NR(84)R(85),
R(84) and R(85) are, independently of each other, H or (C₁-C₄)-alkyl, or, together, can be 4 or 5 methylene groups, of which one CH₂ group can be replaced by oxygen, S, NH, N—CH₃ or N-benzyl, or of which one or two CH₂ groups can be replaced by CH—$C_{dm}H_{2dm+1}$,
and the pharmaceutically tolerated salts thereof,
where, however, compounds are excepted in which the radicals R(1) to R(4) and also HA are combined in the following manner:

| R(1) | R(2) | R(3) | R(4) | HA |
|---|---|---|---|---|
| CON=C(NH₂) | H | H | Et | O |
| CON=C(NH₂) | H | H | Me | O |
| CON=C(NH₂) | H | H | H | O |

Compounds of the formula I are preferred in which:
HA is SO$_m$, O or NR(5),
m is zero, 1 or 2,
R(5) is hydrogen or methyl,
one of the two substituents R(1) and R(2) is

—CO—N=C(NH₂)₂, and whichever is the other is hydrogen, F, Cl, CH₃, —OH or —CO—N=C(NH₂)₂, R(3) is hydrogen, F, Cl, Br, I, —C≡N, $C_q$—$F_{2q+1}$, R(8)-SO₂, R(9)R(10)N—CO, R(11)—CO— or R(12)R(13)N—SO₂—,
where the perfluoroalkyl group is straight-chain or branched,
q is zero, 1, 2, 3, 4, 5 or 6,
R(8), R(9), R(11) and R(12) are, independently, (C₁-C₈)-alkyl, (C₃-C₄)-alkenyl, —$C_nH_{2n}$—R(15) or CF₃,
n is zero, 1, 2, 3 or 4,
R(15) is (C₃-C₆)-cycloalkyl, or phenyl
which is not substituted or is substituted by 1-2 substituents from the group F, Cl, CF₃, methyl, methoxy or NR(16)R(17), with R(16) and R(17) being H or methyl,
where R(9), R(11) and R(12) also have the meaning of H,
R(10) and R(13) are, independently, H or methyl, or R(3) is (C₁-C₈)-alkyl or —$C_{al}H_{2al}$R(18),
al is zero, 1 or 2,
R(18) is (C₃-C₆)-cycloalkyl, or phenyl
which is not substituted or is substituted by 1-2 substituents from the group F, Cl, CF₃, methyl, methoxy or NR(19)R(20), with R(19) and R(20) being H or CH₃;

or

R(3) is quinolyl, isoquinolyl, pyrrolyl, pyridyl or imidazolyl which are linked via C or N and which are unsubstituted or are substituted by 1-2 substituents from the group F, Cl, CF₃, CH₃, methoxy, hydroxyl, amino, methylamino or dimethylamino;

or

R(3) is —C≡CR(56),
R(56) is phenyl,
which is unsubstituted or is substituted by 1-2 substituents from the group F, Cl, CF₃, methyl, methoxy or NR(16)R(17), with R(16) and R(17) being H or CH₃,
R(4) is

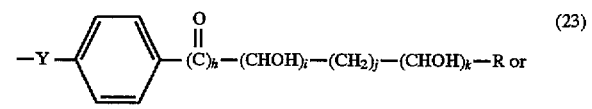 (23)

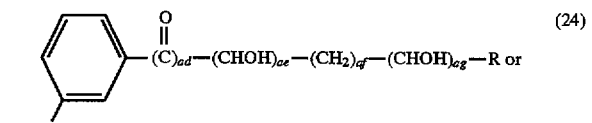 (24)

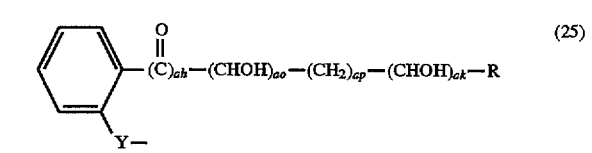 (25)

Y is oxygen, —S— or —NR(22)—,
h, ad and ah are, independently, zero or 1,
i, k, ag, ao and ak are, independently, zero, 1, 2 or 3,
j, af and ap are, independently, zero or 1, where, however, in each case,
h, i and k are not simultaneously zero,
ad, ae and ag are not simultaneously zero, and
ah, ao and ak are not simultaneously zero,
R(23), R(24), R(25) and R(22) are, independently, hydrogen or methyl, or R(4) is hydrogen, F, Cl, Br, CN, (C₁-C₈)-alkyl, $C_q$—$F_{2q+1}$, (C₃-C₈)-alkenyl or —$C_gH_{2g}$R(26),
where the perfluoroalkyl group is straight-chain or branched,
q is zero, 1, 2, 3 or 4,
g is zero, 1 or 2,
R(26) is (C₃-C₈)-cycloalkyl, or phenyl which is not substituted or is substituted by 1-2 substituents from the group F, Cl, CF₃, methyl, methoxy or NR(27)R(28), with R(27) and R(28) being H or CH₃, or R(4) is SR(29), —OR(30), —NR(31)R(32) or —CR(33)R(34)R(35);
R(29), R(30), R(31) and R(33) are, independently, —$C_aH_{2a}$—(C₁-C₉)-heteroaryl, selected from the group consisting of pyrrolyl, imidazolyl, pyrazolyl and pyridyl,
which is unsubstituted or is substituted by 1-2 substituents from the group F, Cl, CF₃, CH₃, methoxy, hydroxyl, amino, methylamino or dimethylamino,
a is zero or 1,
R(32), R(34) and R(35) are, independently of each other, hydrogen or CH₃, or
R(4) is

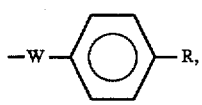 (96)

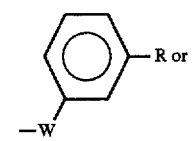 (97)

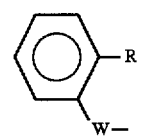 (98)

R(96), R(97) and R(98) are, independently, pyrrolyl, imidazolyl, pyrazolyl or pyridyl,
which, in each case, is unsubstituted or is substituted by 1-2 radicals from the group comprising
F, Cl, $CF_3$, $CH_3$, methoxy, dimethylamino or benzyl,
W is oxygen, S or NR(36)—,
R(36) is H or methyl, or
R(4) is R(37)—$SO_{cm}$ or R(38)R(39)N—$SO_2$—,
R(37) is $(C_1$–$C_6)$-alkyl, $CF_3$, $(C_3$–$C_4)$-alkenyl or —$C_sH_{2s}$—R(40),
s is zero or 1,
R(40) is $(C_3$–$C_6)$-cycloalkyl, or phenyl
which is not substituted or is substituted by 1-2 substituents from the group F, Cl, $CF_3$, methyl, methoxy or NR(41)R(42), with R(41) and R(42) being H or $CH_3$,
R(38) is H, $(C_1$–$C_4)$-alkyl, $CF_3$, $(C_3$–$C_4)$-alkenyl or —$C_wH_{2w}$—R (43),
w is zero or 1
R(43) is $(C_3$–$C_8)$-cycloalkyl, or phenyl
which is not substituted or is substituted by 1-2 substituents from the group F, Cl, $CF_3$, methyl, methoxy or NR(44)R(45), with R(44) and R(45) being H, $(C_1$–$C_4)$-alkyl or $CH_3$,
R(39) is H or $CH_3$,
where R(38) and R(39) can together be 4 or 5 methylene groups, of which one $CH_2$ group can be replaced by oxygen, S, NH, N—$CH_3$ or N-benzyl;

or
R(4) is R(46)X(1)—,
X (1) is oxygen, S, NR(47), (C=O)A— or NR(48)C=MN$^{(*)}$R (49) —,
M is oxygen,
A is oxygen or NR(50),
R(46) is $(C_1$–$C_6)$-alkyl, $(C_3$–$C_4)$-alkenyl, $(CH_2)_bC_dF_{2d+1}$ or —$C_xH_{2x}$—R(51),
b is zero or 1,
d is 1, 2, 3, 4, 5, 6 or 7,
x is zero or 1,
R(51) is $(C_3$–$C_8)$-cycloalkyl, or phenyl
which is not substituted or is substituted by 1-2 substituents from the group F, Cl, $CF_3$, methyl, methoxy or NR(52)R(53); with R(52) and R(53) being H or $CH_3$,
R(47), R(48) and R(50) are hydrogen or $(C_1$–$C_4)$-alkyl.
R(49) is defined as R(46), where R(46) and R(47) and, respectively, R(46) and R(48) can together be 4 or 5 methylene groups, of which one $CH_2$ group can be replaced by oxygen, S, NH, N—$CH_3$ or N-benzyl,
where A and N$^{(*)}$ are bonded to the phenyl nucleus of the benzoylguanidine parent substance;

or
R(4) is —SR(64), —OR(65), —NHR(66), —NR(67)R(68), —CHR(69)R(70),

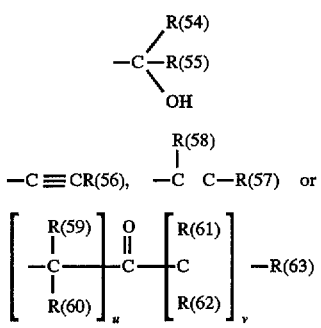

R(64), R(65), R(66), R(67) and R(69) are, identically or differently,
—$(CH_2)_y$—$(CHOH)_z$—$(CH_2)_{aa}$—$(CH_2OH)_t$—R (71) or
—$(CH_2)_{ab}$—O—$(CH_2$—$CH_2O)_{ac}$—R(72),
R(71) and R(72) are hydrogen or methyl,
u is 1 or 2,
v is zero, 1 or 2, y, z and aa are, identically or differently, zero, 1 or 2,
t is 1, 2 or 3,
R(68), R(70), R(54) and R(55) are, identically or differently, hydrogen or $CH_3$, or
R(69) and R(70) and, respectively, R(54) and R(55) are, together with the carbon atom carrying them, a $(C_3$–$C_6)$-cycloalkyl;
R(63) is
H, $(C_1$–$C_4)$-alkyl, $(C_3$–$C_6)$-cycloalkyl or —$C_eH_{2e}$—R(73),
e is zero, 1 or 2,
R(56), R(57) and R(73) are, independently, phenyl
which is unsubstituted or is substituted by 1-2 substituents from the group F, Cl, $CF_3$, methyl, methoxy or NR(74)R(75), with R(74) and R(75) being H or $CH_3$, or
R(56), R(57) and R(73) are, independently, $(C_1$–$C_9)$-heteroaryl, selected from the group consisting of pyrrolyl, imidazolyl, pyrazolyl and pyridyl, which is unsubstituted or is substituted as phenyl;
R(58), R(59), R(60), R(61) and R(62) are hydrogen or methyl, or
R(4) is R(76)—NH—$SO_2$—,
R(76) is R(77)R(78)N—(C=Y')—,
Y' is oxygen, S or N—R(79),
R(77) and R(78) are, identically or differently,
H, $(C_1$–$C_4)$-alkyl, $(C_3$–$C_4)$-alkenyl or —$C_fH_{2f}$—R(80),
f is zero or 1,
R(80) is $(C_5$–$C_7)$-cycloalkyl, or phenyl
which is unsubstituted or is substituted by 1-2 substituents from the group F, Cl, $CF_3$, methoxy or $CH_3$, or R(77) and R(78) together form 4 or 5 methylene groups, of which one CH$_2$ group can be replaced by oxygen, S, NH, N—CH$_3$ or N-benzyl, where
R(79) is defined as R(77), or R(4) is NR(84)R(85),
R(84) and R(85) are, independently of each other, H or (C$_1$-C$_4$)-alkyl, or together form 4 or 5 methylene groups, of which one CH$_2$ group can be replaced by oxygen, S, NH, N—CH$_3$ or N-benzyl, or of which one or two CH$_1$ groups can be replaced by CH—CH$_3$.

Compounds of the formula I are particularly preferred in which:

R(1) is

—CO—N=C(NH$_2$)$_2$

HA is
S, O, NH or NCH$_3$,
and the radicals R(2) to R(4) are combined as follows:

| R(2) | R(3) | R(4) |
|------|------|------|
| H | n-BuNH— | Cl |
| H | H$_2$NSO$_2$— | phenyl-S— |
| H | MeSO$_2$ | phenyl-S— |
| H | pyrrolidin-N— | Me |
| H | pyrrolidin-N— | phenyl-O— |
| H | piperidin-N— | Me |
| H | piperidin-N— | Cl |
| H | pyrrolidin-N— | MeSO$_2$— |
| H | MeSO$_2$ | NH$_2$ |
| H | MeSO$_2$— | cyclopentyl-NH— |
| H | MeSO$_2$— | phenyl-O— |
| H | MeSO$_2$— | (2-Cl-phenyl)-S— |
| H | MeSO$_2$— | (4-MeO-phenyl)-NH— |
| H | MeSO$_2$— | (4-Me-phenyl)-NH— |
| H | MeSO$_2$— | (2,3-diMe-phenyl)-NH— |
| H | Cl— | piperidin-N— |
| H | MeSO$_2$— | (CH$_3$)$_2$—CHCH$_2$—O— |
| H | MeSO$_2$— | (2-OMe-phenyl)-S— |
| H | MeSO$_2$— | (2-Me-phenyl)-S— |
| H | MeSO$_2$— | (2,5-diMe-phenyl)-S— |
| H | pyrrolidin-N— | (2-Cl-phenyl)-O— |
| H | pyrrolidin-N— | (2,3-diCl-phenyl)-O— |
| H | pyrrolidin-N— | (2-CH$_3$-phenyl)-O— |
| H | pyrrolidin-N— | (4-Cl-phenyl)-O— |
| H | pyrrolidin-N— | (2-OMe-phenyl)-O— |

-continued

| R(2) | R(3) | R(4) |
|------|------|------|
| H | pyrrolidin-N-yl | 3-methoxypyridin-N-yl |
| H | MeSO₂— | 2,4-dichloro-3-(methylthio)phenyl |
| H | MeSO₂— | 2,5-dichloro-4-(methylthio)phenyl |
| Me | Me | H |
| H | MeSO₂— | i-Pr |
| H | CF₃ | H |
| H | pyrrol-N-yl | Cl |
| H | MeSO₂— | MeNH— |
| H | MeSO₂— | Et₂N— |
| H | t-Bu | OH |
| H | MeSO₂— | 4-chloro-4-methoxyphenyl |
| H | MeSO₂— | 2-chloro-3-methyl-4-methoxyphenyl |
| H | MeSO₂— | 2-(methylthio)pyridin-N-yl |
| H | MeSO₂— | 3-chloro-5-methoxyphenyl |
| H | MeSO₂— | piperidin-N-yl |
| H | MeSO₂— | 2-Naphthyl |
| H | MeSO₂— | 4-(methylthio)pyridin-N-yl |
| H | pyrrol-N-yl | Me |
| H | pyrrol-N-yl | 2-methyl-3-methoxyphenyl |

-continued

| R(2) | R(3) | R(4) |
|------|------|------|
| H | Cl | Et₂N— |
| H | Me₂N— | H |
| H | MeSO₂— | 3-chloro-2-methoxyphenyl |
| H | Br | NH₂ |
| H | Cl | H |
| H | MeSO₂— | 4-fluoro-4-methoxyphenyl |
| H | MeSO₂— | 4-fluoro-3-chloro-4-methoxyphenyl |
| H | CF₃ | CF₃ |
| H | Me | Me |
| H | I | CF₃ |
| H | Me | H |
| H | H | t-Bu |
| H | MeSO₂— | 4-fluorophenylamino |
| H | Me | Cl |
| H | Br | Me |
| H | Cl | MeO— |
| H | MeCO— | cyclopentyl |
| H | Br | Br |
| H | MeSO₂— | phenylethyl (PhCH₂CH₂—) |
| H | MeSO₂— | phenylethynyl (PhC≡C—) |
| NH₂ | Br | Me |
| H | Me₂N— | t-Bu |
| H | MeSO₂— | 4-hydroxy-4-methoxyphenyl |
| H | pyrrol-N-yl | H |
| H | pyrrol-N-yl | MeO— |
| H | Me | Br |
| H | Cl | F |
| H | t-Bu | H |
| NH₂ | Cl | H |

| R(2) | R(3) | R(4) |
|---|---|---|
| H | pyrrol-1-yl 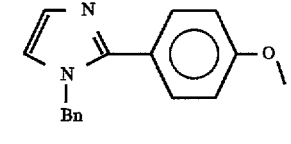 | Me₂N |
| H | Me₂N | Cl |
| H | MeSO₂— | 7-Isoquinolinoxy |
| H | MeSO₂— | 6-quinolinoxy |
| H | MeSO₂— | 4-methoxyphenacyl 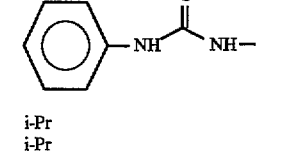 |
| H | MeSO₂— | 1-(4-methoxyphenyl)-1-hydroxyethyl |
| H | MeSO₂— | (CH₃)₂CH—CH₂— |
| H | MeSO₂— | cyclopentyl |
| H | Me₂N— | 4-phenoxyphenyl |
| H | Me₂N— | 4-chloro-2-methoxyphenyl 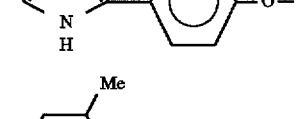 |
| H | Me | Me₂N— |
| H | pyrrol-1-yl | phenoxy |
| H | Me | pyrrol-1-yl |
| H | Cl | i-Pr |
| H | pyrrol-1-yl | i-Pr |
| H | MeSO₂— | 5-quinolinoxy |
| H | cyclopentyl | CF₃ |
| H | i-Pr | MeSO₂— |
| H | i-Pr | CF₃ |
| H | H | i-Pr |
| NH₂ | Br | Br |
| H | MeSO₂— | 1-(4-methoxyphenyl)-1,2-dihydroxypropyl 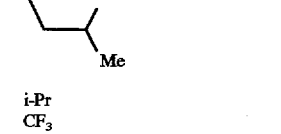 |
| H | pyrrol-1-yl | MeSO₂— |
| H | MeSO₂— | 1-Bn-2-(4-methoxyphenyl)imidazolyl 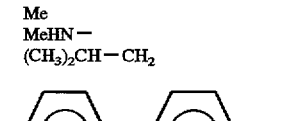 |
| H | Cl | N,N′-diphenylurea 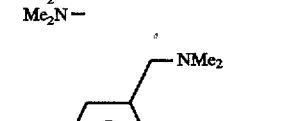 |
| H | Me₂N | i-Pr |
| H | MeHN— | i-Pr |
| H | Cl | Cl |
| H | Me | H₂N— |
| H | Cl | H₂N |
| H | MeSO₂— | 2-(4-methoxyphenyl)imidazolyl |
| H | MeSO₂— | 2,6-dimethylpiperidinyl  |
| H | Me₂N— | i-Pr |
| CF₃ | H | CF₃ |
| H | Br | Me |
| H | Me | Cl |
| H | Me₂N | Me |
| H | CF₃ | MeHN— |
| H | CH₃CO— | (CH₃)₂CH—CH₂ |
| H | MeSO₂— | 4-(pyridin-3-yl)phenoxy 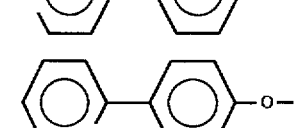 |
| H | CF₃—O— | H |
| H | Me | Me₂N |
| H | Cl | Me₂N— |
| H | MeSO₂— | 5-chloro-2-[(dimethylamino)methyl]phenoxy  |
| H | CH₃CO— | i-Pr |
| H | Br | BnO— |
| H | CF₃ | Br |
| H | i-Pr | MeO— |
| H | MeSO₂— | 4-(pyridin-3-yl)phenoxy |
| H | MeSO₂— | 4-(pyridin-2-yl)phenoxy  |
| H | MeO— | t-Bu |
| H | Br | i-Pr |

-continued

| R(2) | R(3) | R(4) |
|---|---|---|
| CF₃ | H | H |
| H | CF₃ | F |
| H | Ph | CF₃ |
| H | CF₃ | 1-Imidazolyl |
| H | MeCO— | t-Butylmethyl |
| H | Br | F |
| H | Br | MeO— |
| H | CF₃ | PhO— |
| H | CF₃ | Cyclopentyl |
| H | MeSO₂— | Cyclobutyl |
| H | Me | CF₃ |
| H | MeSO₂— | 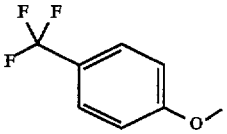 |
| H | OH | t-Butyl |
| H | Cl | OMe |
| H | CF₃ | i-Pr |
| F | CF₃ | H |
| F | H | CF₃ |
| H | t-Butyl | OMe |
| H | MeCO— | 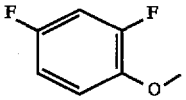 |
| H | MeCO— | 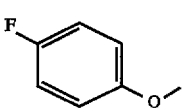 |
| H | t-Butyl | i-Butyl |
| H | CF₃CF₂— | i-Propyl |
| H | CF₃—SO₂— | 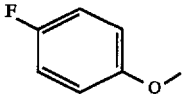 |
| Cl | CF₃ | H |
| Cl | H | CF₃ |
| H | H | Perfluoro-i-propyl |
| H | H | H |
| H | MeSO₂ | 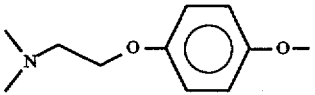 |
| H | H | Perfluoro-n-propyl |
| H | CF₃ | 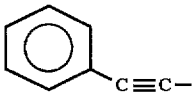 |
| H | CF₃ | 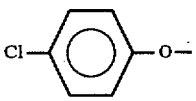 |
| H | CF₃ | 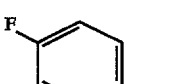 |
| H | F | CF₃ |
| H | MeSO₂— | 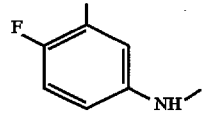 |
| H | t-Butyl | i-Propyl |
| H | t-Butyl | n-Butyl |
| H | i-Propyl | F |
| H | i-Butyl | F |
| H | Cl | 1-Imidazolyl |
| H | H | CF₃—CF₂— |
| H | H | CF₃ |
| H | H | 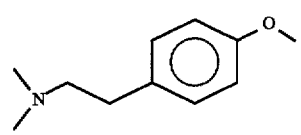 |
| H | MeSO₂ | 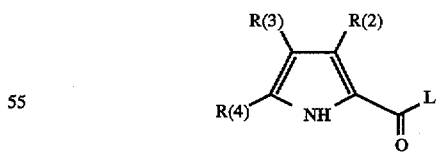 |
| H | CF₃SO₂ | i-propyl |

($C_1$–$C_9$)-Heteroaryl is understood to mean, in particular, radicals which are derived from phenyl or naphthyl and in which one or more CH groups is/are replaced by N, and/or in which at least two adjacent CH groups are replaced (with the formation of a five-membered aromatic ring) by S, NH or O. In addition, one or both atoms of the condensation site of bicyclic radicals may also be N atoms (as in indolizinyl).

Hereroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

If one of the substituents R(1) to R(5) contains one or more centers of asymmetry, these latter can be either in the S or R configuration. The compounds may be present as optical isomers, as diastereomers, as racemates, or as mixtures thereof.

The designated alkyl radicals may be either straight-chain or branched.

The invention furthermore relates to a process for preparing compounds I, wherein compounds of the formula II in which L is a leaving group which can readily be substituted nucleophilically, are reacted with guanidine.

The activated acid derivatives of the formula II in which L is an alkoxy, preferably a methoxy, group, a phenoxy group, a phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which for their part, can be prepared, once again in a manner known per se, from the underlying carboxylic acids (formula II, L=OH), for example using thionyl chloride. In addition to the carbonyl chlorides of the formula II (L=Cl), other activated acid derivatives of the formula II can also be prepared, in a manner known per se, directly from the underlying heteroarylcarboxylic acid derivatives (formula II, L=OH) as can, for example, the methyl esters of the formula II with L =OCH₃ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl—COOC₂H₅ or tosyl chloride in the presence of triethylamine in an inert solvent, in addition to which there is also the activation of heteroarylcarboxylic acids with dicyclohexylcarbodiimide (DCC) or with O-[(cyano (ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for preparing activated carboxylic acid derivatives of the formula II is given, with citation of the source literature, on p. 350 in J. March, Advanced Organic Chemistry, Third Edition (John Wiley & Sons, 1985).

An activated carboxylic acid derivative of the formula I is reacted with guanidine, in a manner known per se, in a protic or aprotic polar, but nevertheless inert, organic solvent. In this context, methanol, isopropanol or THF, at a temperature of from 20° C. up to the boiling temperature of these solvents, have proved of value when reacting the methyl heteroarylcarboxylates (II, L=OMe) with guanidine. Most of the reactions of compounds II with salt-free guanidine were advantageously carried out in inert solvents such as THF, dimethoxyethane, dioxane or isopropanol. However, water can also be used as the solvent.

When L is Cl, the reaction is advantageously carried out with the addition of an acid-capturing agent, for example in the form of excess guanidine, for binding the hydrohalic acid.

Some of the underlying heteroaryl carboxylic acid derivatives of the formula II are known and described in the literature. The unknown compounds of the formula II may be prepared by methods which are known from the literature, by, for example, converting 5-halo-4-chlorosulfonylbenzoic acids, with ammonia or amines, into 4-aminosulfonyl-5-halo-heteroarylcarboxylic acids, or, with a weak reducing agent, such as sodium bisulfite, and subsequent alkylation, into 4-alkylsulfonyl-5-halo-heteroarylcarboxylic acids, and transforming them, by one of the above-described process variants, into compounds I according to the invention.

The introduction of substituted sulfur nucleophiles, oxygen nucleophiles or nitrogen nucleophiles is achieved using methods, which are known from the literature, for nucleophilic substitution in an aromatic compound. In this substitution, halides and trifluoromethanesulfonates have proved to be of value as leaving groups. The reaction is advantageously carried out in a dipolar aprotic solvent, such as, for example, DMF or TMU, at a temperature of between 0° C. and the boiling point of the solvent, preferably between 80° C. and the boiling point of the solvent. An alkali metal salt or alkaline earth metal salt having an anion of high basicity and low nucleophilicity, such as, for example, K₂CO₃, is advantageously used as acid-capturing agent.

The introduction of the alkyl or aryl substituents is achieved by the methods, which are known from the literature, of palladium-mediated cross-coupling of aryl halides with, for example, organozinc compounds, organostannanes, organoboronic acids or organoboranes.

In general, heteroaroylguanidines I are weak bases and can bind acid with the formation of salts. Suitable acid addition salts are the salts of all pharmacologically tolerated acids, for example halides, in particular hydrochlorides, lactates, sulfates, citrates, tartrates, acetates, phosphates, methylsulfonates and p-toluenesulfonates.

It was surprising that, while the compounds according to the invention do not exhibit any undesirable and disadvantageous salidiuretic properties, they do exhibit very good antiarrhythmic properties, as are important for treating diseases which occur, for example, in association with symptoms of oxygen deficiency. As a consequence of their pharmacological properties, the compounds are outstandingly suitable for use as antiarrhythmic pharmaceuticals possessing a cardioprotective component for the prophylaxis and treatment of infarction and for the treatment of angina pectoris, in connection with which they also inhibit or strongly reduce, in a preventive manner, the pathophysiological processes associated with the genesis of ischemically induced damage, in particular associated with the elicitation of ischemically induced cardiac arrhythmias. On account of their protective effects against pathological hypoxic and ischemic situations, the compounds of the formula I according to the invention can, as a consequence of inhibiting the cellular Na⁺/H⁺ exchange mechanism, be used as pharmaceuticals for treating all acute or chronic damage elicited by ischemia, or diseases induced primarily or secondarily thereby. This is the case with regard to their use as pharmaceuticals for surgical interventions, for example in organ transplantations, where the compounds can be used both for protecting the organs in the donor prior to and during removal, for protecting organs which have been removed, for example when they are being treated with or stored in physiological bathing fluids, and when transferring the organs into the recipient. The compounds are likewise valuable protective pharmaceuticals to be used when carrying out angioplastic surgical interventions, for example on the heart or on peripheral vessels. In conformity with their ability to protect against ischemically induced damage, the compounds are also suitable for use as pharmaceuticals for the treatment of ischemias of the nervous system, in particular of the CNS, in connection with which they are suitable, for example, for the treatment of stroke or cerebral edema. Over and above this, the compounds of the formula I according to the invention are also suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the blood vessels. For this reason, the compounds of the formula I are valuable therapeutic agents for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, and against organ hypertrophies or hyperplasias, in particular hyperplasia or hypertrophy of the prostate.

The compounds according to the invention are efficient inhibitors of the cellular sodium/proton antiporter (Na⁺/H⁺ exchanger), which, in numerous diseases (essential hypertension, atherosclerosis, diabetes, etc.), is also elevated in those cells which are readily accessible to measurement, such as, for example, erythrocytes, thrombocytes or leucocytes. The compounds according to the invention therefore represent outstanding and simple scientific tools, for example in their use as diagnostic agents for defining and differentiating particular forms of hypertension and also of atherosclerosis, diabetes, proliferative diseases, etc. In addition to this, the compounds of the formula I can suitably be used in preventive therapy for preventing the genesis of high blood pressure, for example of essential hypertension.

The compounds according to the invention exhibit a solubility in water which is significantly superior to that of the known compounds. For this reason, their suitability for i.v. administration is considerably greater.

In this context, pharmaceuticals which contain a compound I may be administered orally, parenterally, intravenously or rectally, or by inhalation, the preferred route of administration depending on the given features of the disease. In this context, the compounds I may be used either alone or together with pharmaceutical auxiliary substances, both in veterinary and in human medicine.

Owing to his specialist knowledge, the person skilled in the art is familiar with those auxiliary substances which are suitable for the desired pharmaceutical formulation. Antioxidants, dispersants, emulsifiers, defoamers, taste corrigents, preservatives, solubilizers or dyes, for example, can be used in addition to solvents, gel formers, suppository bases, tablet auxiliaries and other active compound excipients.

For a form for oral use, the active compounds are mixed with the additives, such as carrier substances, stabilizers or inert diluents, which are suitable for the purpose, and brought by the customary methods into the forms, such as tablets, coated tablets, hard gelatin capsules, or aqueous, alcoholic or oily solutions, which are suitable for administration. Gum arabic, magnesium oxide, magnesium carbonate, potassium phosphate, lactose, glucose or starch, in particular corn starch, can, for example, be used as inert excipients. In this context, the preparation can be effected either as a dry granulate or as a wet granulate. Vegetable or animal oils, for example, such as sunflower oil or cod-liver oil, are suitable for use as oily excipients or as solvents.

For subcutaneous or intravenous administration, the active compounds are brought into solution, suspension or emulsion, if desired using the substances, such as solubilizers, emulsifiers or other auxiliary substances, which are customary for the purpose. Examples of suitable solvents are: water, physiological sodium chloride solution or alcohols, for example ethanol, propanol or glycerol, as well as sugar solutions, such as glucose or mannitol solutions, or else a mixture of the different solvents mentioned.

Solutions, suspensions or emulsions of the active compound of the formula I in a pharmaceutically harmless solvent, such as, in particular, ethanol or water, or in a mixture of such solvents, represent examples of suitable pharmaceutical formulations for administration in the form of aerosols or sprays. As required, the formulation can also contain additional pharmaceutical auxiliary substances such as surfactants, emulsifiers and stabilizers, as well as a propellent gas. Such a preparation customarily contains the active compound in a concentration of from about 0.1 to 10, in particular of from about 0.3 to 3, % by weight.

The dosage of the active compound of the formula I to be administered, and the frequency of administration, depend on the strength and duration of the effect of the compounds used; additionally also on the nature and severity of the disease to be treated and on the sex, age, weight and individual responsiveness of the mammalian subject to be treated.

On average, the daily dose of a compound of the formula I is, for a patient of approximately 75 kg in weight, at least 0.001 mg, preferably 0.01 mg to 10 mg, preferably 1 mg. In acute manifestations of the disease, for example immediately after suffering a cardiac infarction, even greater and, in particular, more frequent dosages may also be necessary, for example up to 4 individual doses per day. In the case of i.v. use in particular, for example in an infarction patient in intensive care, up to 100 mg per day may be necessary.

The novel compounds of the formula I which are listed below, and their physiologically tolerated salts, can be prepared in analogy with the instructions given in the exemplary embodiments:

List of abbreviations:

| | |
|---|---|
| MeOH | methanol |
| DMF | N,N-dimethylformamide |
| TMU | N,N,N',N'-tetramethylurea |
| NBS | N-bromosuccinimide |
| AIBN | α,α-azobis(isobutyronitrile) |
| EI | electron impact |
| DCI | desorption chemical ionisation |
| RT | room temperature |
| EA | ethyl acetate (EtOAc) |
| DIP | diisopropyl ether |
| MTB | methyl tert-butyl ether |
| mp | melting point |
| HEP | n-heptane |
| DME | dimethoxyethane |
| FAB | fast atom bombardment |
| $CH_2Cl_2$ | dichloromethane |
| THF | tetrahydrofuran |
| eq | equivalent |
| ES | electrostatic spray ionization |
| Me | methyl |
| Et | ethyl |
| Bn | benzyl |
| CNS | central nervous system |
| brine | saturated aqueous solution of NaCl |

Experimental Section

EXAMPLE 1

5-Heptafluoroisopropyl-1-methylpyrrole-2-carboguanidide a) Methyl 5-heptafluoroisopropyl-1-methylpyrrole-2-carboxylate 1.1 g of methyl 1-methylpyrrole-2-carboxylate, 1.7 ml of perfluorooisopropyl iodide and 1.3 g of $FeSO_4 \times 7\ H_2O$ are initially introduced in 80 ml of DMSO, and 4.1 ml of $H_2O_2$ (35%) are slowly added dropwise at RT. The mixture is stirred at RT for 1.5 h and then extracted 3× with 200 ml of MTB on each occasion, and the organic phase is additionally washed 1× with 100 ml of water and 2× with 100 ml of brine. Drying takes place over $Na_2SO_4$ and the solvent is removed in vacuo. Chromatography using EA/HEP ¼ gives 310 mg of a colorless oil.

$R_f$ (EA/HEP 1/4) = 0.62    MS (DCI): 308 $(M + H)^+$ b) 5-Heptafluoroisopropyl-1-methylpyrrole-2-carboguanidide 310 mg of methyl 5-heptafluoroisopropyl-1-methylpyrrole-2-carboxylate and 295 mg of guanidine are boiled under reflux, for 4 h, in 5 ml of anhydrous isopropanol. The solvent is removed in vacuo and the residue is chromatographed using EA. 123 mg of a colorless oil are obtained.

$R_f$ (EA) = 0.26   MS (ES): 335 (M + H)$^+$

Conversion into the hydrochloride yields white crystals, mp 165° C.

The title compounds in Examples 2–5 are synthesized in analogy with Example 1:

EXAMPLE 2

5-Heptafluoro-n-propyl-1-methylpyrrole-2-carboguanidide $R_f$ (EA) = 0.20   MS (ES): 335 (M + H)$^+$ mp (hydrochloride): 207° C.

EXAMPLE 3

5-Pentafluoroethyl-1-methylpyrrole-2-carboguanidide $R_f$ (EA) = 0.16   MS (DCI): 285 (M + H)$^+$ mp (hydrochloride):210° C.

EXAMPLE 4

5-Trifluoromethyl-1-methylpyrrole-2-carboguanidide $R_f$ (EA) = 0.16   MS (DCI): 235 (M + H)$^+$ mp (hydrochloride): 230° C.

EXAMPLE 5

1-Methylpyrrole-2-carboguanidide $R_f$ (EA/MeOH 10:1) = 0.13   MS (ES): 167 (M + H)$^+$ mp (hydrochloride): 255° C.

EXAMPLE 6

5-Isopropyl-4-methylsulfonylthiophene-2-carboguanidide a) 5-bromothiophene-2-carboxylic acid 10 g of thiophene-2-carboxylic acid are dissolved 100 ml of acetic acid and 100 ml of water, and a solution of 4 ml of bromine in 50 ml of acetic acid and 50 ml of water is added dropwise, at 0° C., over a period of one hour. The mixture is subsequently stirred at 0° C. for 1 h and the product is then filtered off with suction and recrystallized from water. 4.8 g of colorless crystals are obtained, mp 140° C.

$R_f$ (MTB 2% HOAc) = 0.54   MS (DCI): 207 (M + H)$^+$ b) 5-Bromo-4-chlorosulfonylthiophene-2-carboxylic acid 37 g of 5-bromothiophene-2-carboxylic acid are dissolved, at RT, in 133 ml of chlorosulfonic acid, and this mixture is stirred at 100° C. for 45 min. The mixture is subsequently poured onto 1 kg of ice and the product is filtered off with suction. 53 g of a colorless solid are obtained, mp 96° C.

$R_f$ (MTB 2% HOAc) = 0.3   MS (DCI): 305 (M + H)$^+$ c) 5-Bromo-4-hydroxysulfinylthiophene-2-carboxylic acid 27.5 g of sodium sulfite are dissolved in 300 ml of water, and a total of 35 g of 5-bromo-4-chlorosulfonylthiophene-2-carboxylic acid is added, in portions, at 70° C., with a pH of 9–11 being maintained using 10N NaOH. The mixture is subsequently stirred at 70° C. for 2 h and then adjusted to pH=1 with HCl, after which the product is filtered off with suction. 41 g of colorless crystals are obtained.

mp 195° C. (decomposition)

d) 5-Bromo-4-hydroxysulfinylthiophene-2-carboxylic acid, disodium salt 41 g of 5-bromo-4-hydroxysulfinylthiophene-2-carboxylic acid are suspended in 150 ml of water, and 90 ml of 2N NaOH are added (pH=10). The water is removed in vacuo, the residue is stirred up in 1 l of acetone, and the product is filtered off with suction. 46 g are obtained of a colorless, amorphous solid, which is immediately subjected to further reaction.

e) Methyl 5-bromo-4-methylsulfonylthiophene-2-carboxylate 46 g of the title compound 6 d) are suspended in 150 ml of DMF, and 32 ml of methyl iodide are added. The mixture is stirred at 50° C. for 5 h and then poured onto 1 l of waters the product is filtered off with suction. 35 g of a colorless solid are obtained, mp 135° C.

$R_f$ (DIP) = 0.20   MS (DCI): 299 (M + H)$^+$ f) Methyl 5-isopropyl-4-methylsulfonylthiophene-2-carboxylate 30 ml of a 2M solution of isopropylmagnesium chloride in THF are added to 140 ml of a 0.5M solution of zinc chloride in THF. The mixture is stirred at 50° C. for 5 h and the resulting isopropylzinc derivative undergoes further use as solution A. 6 g of methyl 5-bromo-4-methylsulfonylthiophene-2-carboxylate, 0.6 g of [1,1'-bis(diphenylphosphino)ferrocene]Pd(II)Cl$_2$×CH$_2$Cl$_2$ and 180 mg of CuI are stirred, at RT for 10 min, in 100 ml of anhydrous THF, and solution A is subsequently added dropwise. The mixture is subsequently stirred at RT for 18 h, and the solvent is then removed in vacuo. The residue is suspended in 200 ml of a saturated aqueous solution of NaHSO$_4$, and this suspension is extracted 3× with 200 ml of EA on each occasion. Drying takes place over Na$_2$SO$_4$, the solvent is removed in vacuo, and the residue is chromatographed using once in each case, DIP and EA/HEP 1:3. 1.7 g of a colorless oil are obtained.

$R_f$ (DIP) = 0.29   $R_f$ (EA/HEP 1:3) = 0.32

MS(DCI): 263 (M+H)$^+$ g) 5-Isopropyl-4-methylsulfonylthiophene-2-carboguanidide 700 mg of methyl 5-isopropyl-4-methylsulfonylthiophene-2-carboxylate and 790 mg of guanidine are dissolved in 5 ml of anhydrous isopropanol, and this mixture is boiled under reflux for 1 h. The solvent is removed in vacuo and 80 ml of water are added; the mixture is adjusted to pH=2 with aqueous HCl, and the product is filtered off. The precipitate is dissolved in 50 ml of a saturated aqueous solution of Na$_2$CO$_3$, and this solution is extracted 3× with 50 ml of EA on each occasion. The organic phase is dried over Na$_2$SO$_4$, and the solvent is removed in vacuo. 850 mg of an amorphous solid are obtained.

$R_f$ (MeOH/EA 1:10) = 0.41   MS (ES): 290 (M + H)$^+$ mp (hydrochloride): 267° C.
mp (methanesulfonate): 128° C.

The title compounds of Examples 7, 8 and 10 were synthesized in analogy with Example 6 g):

EXAMPLE 7

5Methylthiophene-2-carboguanidide mp (hydrochloride): 236° C.  MS (DCI): 184 (M + H)+

EXAMPLE 8

4,5-Dibromothiophene-2-carboguanidide mp (hydrochloride): 268° C.  MS (DCI): 326 (M + H)+

EXAMPLE 9

4-Isopropyl-5-methylsulfonylthiophene-2-carboguanidide a) 4-Bromo-5-methylthiothiophene-2-carboxylic acid 25 g of 4,5-dibromothiophenecarboxylic acid, 12.2 g of NaSCH₃ and 60 g of K₂CO₃ are stirred, at 120° C. for 5 h, in 1 l of DMF. This mixture is then poured onto 3 l of water, and the pH of the resulting mixture is adjusted to 1 with HCl; the product is filtered off with suction and used for further reaction without purification.

Yield: 14 g of amorphous powder.

$R_f$(DIP 2% HOAc)=0.46 b) 4-Bromo-5-methylsulfonylthiophene-2-carboxylic acid 14 g of the methylthio compound 9 a) are dissolved in 500 ml of CH₂Cl₂, and 41 g of m-chloroperbenzoic acid are then added in portions. The mixture is stirred at RT for 1.5 h, and the solvent is then removed in vacuo and the product is esterified without purification.

$R_f$(DIP 2% HOAc)=0.10 c) Methyl 4-bromo-5-methylsulfonylthiophene-2-carboxylate 50 ml of SOCl₂ are added to the whole of the crude product from Example 9 b) in 200 ml of MeOH, and this mixture is boiled under reflux for 5 h. Excess SOCl₂ and the solvent are removed in vacuo and the residue is chromatographed using DIP. 11 g of a colorless oil are obtained.

$R_f$ (DIP) = 0.28  MS (DCI): 299 (M + H)+ d) Methyl 4-isopropyl-5-methylsulfonylthiophene-2-carboxylate 30 ml of a 2M solution of isopropylmagnesium chloride in diethyl ether are added dropwise to a 1M solution of ZnCl₂ in diethyl ether, and this mixture is boiled under reflux for 6 h. (Solution A)

6 g of the bromide 9 c), 588 mg of [1,1-bis(diphenylphosphino)ferrocene]Pd(II)Cl₂ and 183 mg of CuI are stirred, at RT for 10 min, in 100 ml of THF, and solution A is then added to this mixture. The resulting mixture is stirred at RT for 19 h, and 200 ml of EA are then added; the resulting mixture is washed 1× with 200 ml of water and 1× with 200 ml of brine. The solvent is removed in vacuo and the residue is chromatographed using EA/HEP 1:2.

2 g of a colorless oil are obtained.

$R_f$ (EA/HEP 1:2) = 0.25  MS (DCI): 263 (M + H)+ e) 4-Isopropyl-5-methylsulfonylthiophene-2-carboguanidide 1 g of the methyl ester 9 d) is reacted with 1.1 g of guanidine in analogy with Example 6 g). 900 mg of an amorphous powder are obtained.

$R_f$ (EA/MeOH 10:1) = 0.41  MS (ES): 290 (M + H)+

The compound is converted into the methanesulfonate, mp=210° C.

EXAMPLE 10

3-Methylthiophene-2-carboguanidide mp (hydrochloride): 232° C.  MS (DCI): 184 (M + H)+

Pharmacological data

Inhibition of the Na⁺/H⁺ exchanger of rabbit erythrocytes

New Zealand White rabbits (Ivanovas) were given a standard diet containing 2% cholesterol for six weeks in order to activate Na⁺/H⁺ exchange and thus to be able to use flame photometry to determine the Na⁺ influx into the erythrocytes via Na⁺/H⁺ exchange. The blood was removed from the aural arteries and rendered incoagulable by the addition of 25 IU of potassium heparin. One part of each sample was used for the duplicate determination of the hematocrit by centrifugation. Aliquots of in each case 100 µl were employed for measuring the initial content of Na⁺ in the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl)aminomethane). The erythrocytes were then washed three times with ice cold MgCl₂/ouabain solution (mmol/l: 112 MgCl₂, 0.1 ouabain) and hemolyzed in 2.0 ml of distilled water. The intracellular content of sodium was determined by flame photometry.

The nett influx of Na⁺ was calculated from the difference between the initial sodium values and the sodium content of the erythrocytes following incubation. The amiloride-inhibitable sodium influx was given by the difference in the sodium content of the erythrocytes following incubation with and without $3 \times 10^{-4}$ mol/l amiloride. The same procedure was also used in the case of the compounds according to the invention.

Results

| Example | IC₅₀ [µmol/l] |
| --- | --- |
| 1 | 0.3 |
| 2 | 1.0 |
| 3 | 0.3 |
| 4 | 0.2 |
| 5 | 5.0 |
| 6 | 0.5 |
| 7 | 3 |
| 8 | 0.5 |

We claim:

1. A heteroaroylguanidine of the formula I

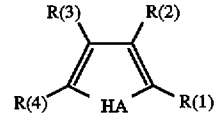

in which:

HA is $SO_m$, m is zero, 1 or 2, one of the two substituents R(1) and R(2)

is $-CO-N=C(NH_2)_2$, and whichever is the other is
hydrogen, F, Cl, Br, I, $(C_1-C_3)$-alkyl, $-OR(6)$, $C_rF_{2r+1}$, $-CO-N=C(NH_2)_2$ or $-NR(6)R(7)$,
R(6) and R(7) are, independently, hydrogen or $(C_1-C_3)$-alkyl,
r is 1, 2, 3 or 4, R(3) and R(4) are, independently of each other, hydrogen, F, Cl, Br, I, $-C\equiv N$, $X-(CH_2)_p-(C_q-F_{2q+1})$, R(8) $-SO_{bm}$, $R(9)R(10)N-CO$, $R(11)-CO-$ or $R(12)R(13)N-SO_2-$,
where the perfluoroalkyl group is straight-chain or branched,
X is oxygen, S or NR(14), R(14) is H or $(C_1-C_3)$-alkyl,
bm is zero, 1 or 2,
p is zero, 1 or 2,
q is zero, 1, 2, 3, 4, 5 or 6,
R(8), R(9), R(11) and R(12) are, independently, $(C_1-C_8)$-alkyl, $(C_3-C_6)$-alkenyl, $-C_nH_{2n}-$ R(15) or $CF_3$,
n is zero, 1, 2, 3 or 4,
R(15) is $(C_3-C_7)$-cycloalkyl, or phenyl which is not substituted or is substituted by 1–3 substituents selected from the group F, Cl, $CF_3$, methyl, methoxy or $NR(16)R(17)$ with R(16) and R(17) being H or $C_1-C_4$-alkyl,
where R(9), R(11) and R(12) also have the meaning of H,
R(10) and R(13) are, independently, H or $(C_1-C_4)$-alkyl,
where R(9) and R(10) and also R(12) and R(13) can together be 4 or 5 methylene groups, of which one $CH_2$ group can be replaced by oxygen, S, NH, $N-CH_3$ or N-benzyl, or R(3) and R(4) are, independently of each other, $(C_1-C_8)$-alkyl or $-C_{al}H_{2al}R(18)$,
al is zero, 1 or 2,
R(18) is $(C_3-C_8)$-cycloalkyl, or phenyl which is not substituted or is substituted by 1–3 substituents from the group F, Cl, $CF_3$, methyl, methoxy or $NR(19)R(20)$, with R(19) and R(20) being H or $CH_3$;

or

R(3) and R(4) are, independently of each other, $(C_1-C_9)$-heteroaryl,
which is linked via C or N and which is unsubstituted or is substituted by 1–3 substituents from the group F, Cl, $CF_3$, $CH_3$, methoxy, hydroxyl, amino, methylamino or dimethylamino;

or

R(3) and R(4) are, independently of each other,

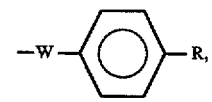
(23)

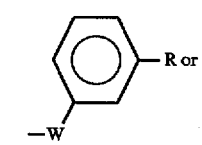
(24)

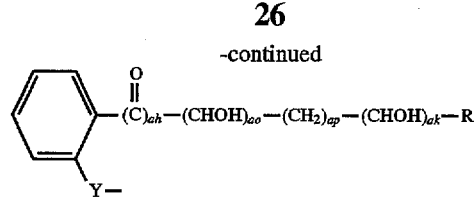
(25)

Y is oxygen, $-S-$ or $-NR(22)-$,
h, ad and ah are, independently, zero or 1,
i, j, k, ae, af, ag, ao, ap and ak are, independently, zero, 1, 2, 3 or 4,
where, however, in each case,
h, i and k are not simultaneously zero,
ad, ae and ag are not simultaneously zero, and
ah, ao and ak are not simultaneously zero,
R(23), R(24), R(25) and R(22) are, independently, hydrogen or $(C_1-C_3)$-alkyl, or R(3) and R(4) are, independently of each other, hydrogen, F, Cl, Br, I, CN, $(C_1-C_8)$-alkyl, $(C_1-C_8)$-perfluoroalkyl, $(C_3-C_8)$-alkenyl or $-C_gH_{2g}R(26)$,
g is zero, 1, 2, 3 or 4,
R(26) is $(C_3-C_8)$-cycloalkyl, phenyl, biphenylyl or naphthyl,
where the aromatic radicals are not substituted or are substituted by 1–3 substituents from the group F, Cl, $CF_3$, methyl, methoxy or $NR(27)R(28)$, with R(27) and R(28) being H, $(C_1-C_4)$-alkyl or $(C_1-C_4)$-perfluoroalkyl;

or

R(3) and R(4) are, independently of each other,
SR(29), $-OR(30)$, $-NR(31)R(32)$ or $-CR(33)R(34)R(35)$;
R(29), R(30), R(31) and R(33) are, independently, $-C_aH_{2a}-(C_1-C_9)$-heteroaryl
which is unsubstituted or is substituted by 1–3 substituents from the group F, Cl, $CF_3$, $CH_3$, methoxy, hydroxyl, amino, methylamino or dimethylamino, a is zero, 1 or 2,
R(32), R(34) and R(35) are, independently of each other, defined as R(29), or are hydrogen, $(C_1-C_4)$-alkyl or $(C_1-C_4)$-perfluoroalkyl;

or

R(3) and R(4) are, independently of each other,

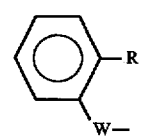
(96)

(97)

(98)

R(96), R(97) and R(98) are, independently, $(C_1-C_9)$-heteroaryl,
which is linked via C or N and which is unsubstituted or is substituted by 1–3 substituents from the group F, Cl, $CF_3$, $CH_3$, methoxy, hydroxyl, amino, methylamino, dimethylamino or benzyl,
W is oxygen, S or NR(36)—, R(36) is H or (C₁-C₄)-alkyl, or R(3) and R(4) are, independently of each other, R(37)—SO_cm or R(38)R(39)N—SO₂—,
cm is 1 or 2,
R(37) is (C₁-C₈)-alkyl, (C₁-C₈)-perfluoroalkyl, (C₃-C₈)-alkenyl or —C_sH_{2s}—R(40),
s is zero, 1, 2, 3 or 4,
R(40) is (C₃-C₈)-cycloalkyl, phenyl, biphenylyl or naphthyl,
where the aromatic radicals are not substituted or are substituted by 1-3 substituents from the group F, Cl, CF₃, methyl, methoxy or NR(41) R(42), with R(41) and R(42) being H, (C₁-C₄)-alkyl or (C₁-C₄)-perfluoroalkyl;
R(38) is H, (C₁-C₈)-alkyl, (C₁-C₈)-perfluoroalkyl, (C₃-C₈)-alkenyl or —C_wH_{2w}—R(43),
w is zero, 1, 2, 3 or 4,
R(43) is (C₃-C₈)-cycloalkyl, phenyl, biphenylyl or naphthyl where the aromatic radicals are not substituted or are substituted by 1-3 substituents from the group F, Cl, CF₃, methyl, methoxy or NR(44) R(45), with R(44) and R (45) being H, (C₁-C₄)-alkyl or (C₁-C₄)-perfluoroalkyl,
R(39) is H, (C₁-C₄)-alkyl or (C₁-C₄)-perfluoroalkyl, where R(38) and R(39) can together be 4 or 5 methylene groups, of which one CH₂ group can be replaced by oxygen, S, NH, N—CH₃ or N-benzyl;

or

R(3) and R(4) are, independently of each other, R(46)X(1)—,

X(1) is oxygen, S, NR (47), (D=O) A— or

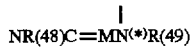

M is oxygen or S,
A is oxygen or NR(50),
D is C or SO,
R(46) is (C₁-C₈)-alkyl, (C₃-C₈)-alkenyl, (CH₂)_b C_dF_{2d+1} or —C_xH_{2x}—R(51),
b is zero or 1,
d is 1, 2, 3, 4, 5, 6 or 7,
x is zero, 1, 2, 3 or 4,
R(51) is (C₃-C₈)-cycloalkyl, phenyl, biphenylyl, naphthyl,
where the aromatic radicals are not substituted or are substituted by 1-3 substituents from the group F, Cl, CF₃, methyl, methoxy or NR(52)R(53); with R(52) and R(53) being H, (C₁-C₄)-alkyl or (C₁-C₄)-perfluoroalkyl;
R(47), R(48) and R(50) are, independently, hydrogen, (C₁-C₄)-alkyl or (C₁-C₄)-perfluoroalkyl,
R(49) is defined as R(46), where
R(46) and R(47) and, respectively, R(46) and R(48) can together be 4 or 5 methylene groups, of which one CH₂ group can be replaced by oxygen, S, NH, N—CH₃ or N-benzyl,
where A and N^{(*)} are bonded to the phenyl nucleus of the heteroaroylguanidine parent substance;

or

R(3) and R(4) are, independently of each other, —SR(64), —OR(65), —NHR(66), —NR(67)R(68), —CHR(69)R(70),

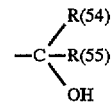

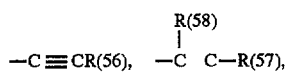

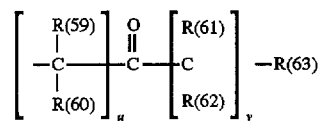

R(64), R(65), R(66), R(67) and R(69) are, identically or differently,
—(CH₂)_y—(CHOH)_z—(CH₂)_{aa}—(CH₂OH)_t—R(71) or
—(CH₂)_{ab}—O—(CH₂—CH₂O)_{ac}—R(72),
R(71) and R(72) are hydrogen or methyl,
u is 1, 2, 3 or 4,
v is zero, 1, 2, 3 or 4, y, z and aa are, identically or differently, zero, 1, 2, 3 or 4,
t is 1, 2, 3 or 4,
R(68), (R70), R(54) and R(55) are, identically or differently, hydrogen or (C₁-C₆)-alkyl, or
R(69) and R(70) and, respectively, R(54) and R(55) are, together with the carbon atom carrying them, a (C₃-C₈)-cycloalkyl;
R(63) is
H, (C₁-C₈)-alkyl, (C₃-C₈)-cycloalkyl or —C_eH_{2e}—R(73),
e is zero, 1, 2, 3 or 4,
R(56), R(57) and R(73) are, independently, phenyl,
which is unsubstituted or is substituted by 1-3 substituents from the group F, Cl, CF₃, methyl, methoxy or NR(74)R(75) with R(74) and R(75) being H or (C₁-C₄)-alkyl,
or R(56), R(57) and R(73) are, independently, (C₁-C₉)-heteroaryl,
which is unsubstituted or is substituted with phenyl;
R(58), R(59), R(60), R(61) and R(62) are hydrogen or methyl, or R(3) and R(4) are, independently of each other, R(76)—NH—SO₂—,
R(76) is R(77)R(78)N—(C=Y')—,
Y' is oxygen, S or N—R(79),
R(77) and R(78) are, identically or differently,
H, (C₁-C₈)-alkyl, (C₃-C₆)-alkenyl, or —C_fH_{2f}—R(80),
f is zero, 1, 2, 3 or 4,
R (80) is (C₅-C₇)-cycloalkyl, or phenyl
which is unsubstituted or is substituted by 1-3 substituents from the group F, Cl, CF₃, methoxy or (C₁-C₄)-alkyl, or R(77) and R(78) together form 4 or 5 methylene groups, of which one CH₂ group can be replaced by oxygen, S, NH, N—CH₃ or N-benzyl, where R(79) is defined as R(77) or amidine;

or

R(3) and R(4) are, independently of each other, NR(84)R(85),
R(84) and R(85) are, independently of each other,
H or (C₁-C₄)-alkyl, or, together, can be 4 or 5 methylene groups, of which one CH₂ group can be replaced by oxygen, S, NH, N—CH₃ or N-benzyl, or of which one or two $CH_2$ groups can be replaced by $CH-C_{dm}H_{2dm+1}$,
and the pharmaceutically tolerated salts thereof.

2. A heteroaroylguanidine I as claimed in claim 1, wherein:

HA is $SO_m$,
m is zero, 1 or 2,
one of the two substituents R(1) and R(2) is

—CO—N=C(NH$_2$)$_2$, and whichever is the other is hydrogen, F, Cl, $CH_3$, —OH or —CO—N=C (NH$_2$)$_2$, R(3) is hydrogen, F, Cl, Br, I, —C≡N, X—$(CH_2)_p$—$(C_q-F_{2q+1})$, R(8)—$SO_2$,
R(9)R(10)N—CO, R(11)—CO— or R(12)R(13)N—$SO_2$—,
where the perfluoroalkyl group is straight-chain or branched,
q is zero, 1, 2, 3, 4, 5 or 6,
R(8), R(9), R(11) and R(12) are, independently, $(C_1-C_8)$-alkyl, $(C_3-C_4)$-alkenyl, —$C_nH_{2n}$—R(15) or $CF_3$,
n is zero, 1, 2, 3 or 4,
R(15) is $(C_3-C_6)$-cycloalkyl, or phenyl
which is not substituted or is substituted by 1–2 substituents from the group F, Cl, $CF_3$, methyl, methoxy or NR(16)R(17), with R(16) and R(17) being H or methyl,
where R(9), R(11) and R(12) also have the meaning of H,
R(10) and R(13) are, independently, H or methyl, or R(3) is $(C_1-C_8)$-alkyl or —$C_{al}H_{2al}$R(18), al is zero, 1 or 2,
R(18) is $(C_3-C_6)$-cycloalkyl, or phenyl
which is not substituted or is substituted by 1–2 substituents from the group F, Cl, $CF_3$, methyl, methoxy or NR(19)R(20), with R(19) and R(20) being H or $CH_3$, or R(3) is quinolyl, isoquinolyl, pyrrolyl, pyridyl or imidazolyl which are linked via C or N and which are unsubstituted or are substituted by 1–2 substituents from the group F, Cl, $CF_3$, $CH_3$, methoxy, hydroxyl, amino, methylamino or dimethylamino;

or

R(3) is —C≡CR(56),
R(56) is phenyl,
which is unsubstituted or is substituted by 1–2 substituents from the group F, Cl, $CF_3$, methyl, methoxy or NR(16)R(17), with R(16) and R(17) being H or $CH_3$,
R(4) is

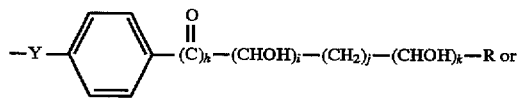  (23)

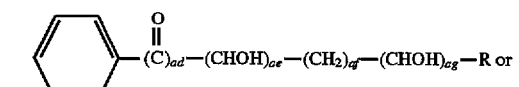  (24)

  (25)

Y is oxygen, —S— or —NR(22)—,
h, ad and ah are, independently, zero or 1,
i, k, ag, ao and ak are, independently, zero, 1, 2 or 3,
j, af and ap are, independently, zero or 1,
where, however, in each case,
h, i and k are not simultaneously zero,
ad, ae and ag are not simultaneously zero, and
ah, ao and ak are not simultaneously zero,
R(23), R(24), R(25) and R(22) are, independently, hydrogen or methyl, or R(4) is hydrogen, F, Cl, Br, CN, $(C_1-C_8)$-alkyl, $C_q$—$F_{2q+1}$, $(C_3-C_8)$-alkenyl or —$C_gH_{2g}$R(26),
where the perfluoroalkyl group is straight-chain or branched,
q is zero, 1, 2, 3 or 4,
g is zero, 1 or 2,
R(26) is $(C_3-C_8)$-cycloalkyl, or phenyl
which is not substituted or is substituted by 1–2 substituents from the group F, Cl, $CF_3$, methyl, methoxy or NR(27)R(28), with R(27) and R(28) being H or $CH_3$, or R(4) is SR(29), —OR(30), —NR(31)R(32) or —CR(33)R(34)R(35);
R(29), R(30), R(31) and R(33) are, independently, —$C_aH_{2a}$—$(C_1-C_9)$-heteroaryl, selected from the group consisting of pyrrolyl, imidazolyl, pyrazolyl and pyridyl,
which is unsubstituted or is substituted by 1–2 substituents from the group F, Cl, $CF_3$, $CH_3$, methoxy, hydroxyl, amino, methylamino or dimethylamino,
a is zero or 1,
R(32), R(34) and R(35) are, independently of each other,
hydrogen or $CH_3$, or R(4) is

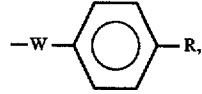  (96)

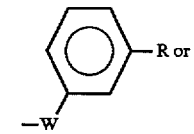  (97)

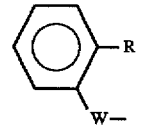  (98)

R(96), R(97) and R(98) are, independently, pyrrolyl, imidazolyl, pyrazolyl or pyridyl,
which, in each case, is unsubstituted or is substituted by 1–2 radicals from the group comprising F, Cl, $CF_3$, $CH_3$, methoxy, dimethylamino or benzyl, W is oxygen, S or NR(36)—,
R(36) is H or methyl, or R(4) is R(37)—SO$_{cm}$ or R(38)R(39)N—SO$_2$—,
R(37) is (C$_1$-C$_6$)-alkyl, CF$_3$, (C$_3$-C$_4$)-alkenyl or —C$_s$H$_{2s}$—R(40),
cm is 1 or 2;
s is zero or 1,
R(40) is (C$_3$-C$_6$)-cycloalkyl, or phenyl
which is not substituted or is substituted by 1-2 substituents from the group F, Cl, CF$_3$, methyl, methoxy or NR(41)R(42), with R(41) and R(42) being H or CH$_3$,
R(38) is H, (C$_1$-C$_4$)-alkyl, CF$_3$, (C$_3$-C$_4$)-alkenyl or —C$_w$H$_{2w}$—R(43),
w is zero or 1
R(43) is (C$_3$-C$_8$)-cycloalkyl, or phenyl
which is not substituted or is substituted by 1-2 substituents from the group F, Cl, CF$_3$, methyl, methoxy or NR(44)R(45), with R(44) and R(45) being H, (C$_1$-C$_4$)-alkyl or CH$_3$,
R(39) is H or CH$_3$,
where R(38) and R(39) can together be 4 or 5 methylene groups, of which one CH$_2$ group can be replaced by oxygen, S, NH, N—CH$_3$ or N-benzyl;

or

R(4) is R(46)X(1)—,
X(1) is oxygen, S, NR(47), (C=O)A— or

NR(48)C=MN$^{(*)}$R(49)

M is oxygen,
A is oxygen or NR(50),
R(46) is (C$_1$-C$_6$)-alkyl, (C$_3$-C$_4$)-alkenyl, (CH$_2$)$_b$C$_d$F$_{2d+1}$ or —C$_x$H$_{2x}$—R(51),
b is zero or 1,
d is 1, 2, 3, 4, 5, 6 or 7,
x is zero or 1,
R(51) is (C$_3$-C$_8$)-cycloalkyl, or phenyl
which is not substituted or is substituted by 1-2 substituents from the group F, Cl, CF$_3$, methyl, methoxy or NR(52)R(53); with R(52) and R(53) being H or CH$_3$,
R(47), R(48) and R(50) are hydrogen or (C$_1$-C$_4$)-alkyl,
R(49) is defined as R(46), where
R(46) and R(47) and, respectively, R(46) and R(48) can together be 4 or 5 methylene groups, of which one CH$_2$ group can be replaced by oxygen, S, NH, N—CH$_3$ or N-benzyl, where A and N$^{(*)}$ are bonded to the phenyl nucleus of the heteroaroylguanidine parent substance;

or

R(4) is —SR(64), —OR(65), —NHR(66), —NR(67)R(68), —CHR(69)R(70),

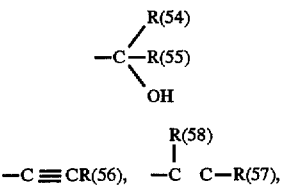
—C≡CR(56), —C C—R(57),

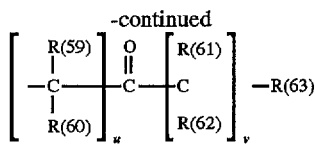
—R(63)

R(64), R(65), R(66), R(67) and R(69) are, identically or differently,
—(CH$_2$)$_y$—(CHOH)$_z$—(CH$_2$)$_{aa}$—(CH$_2$OH)$_t$—R(71) or —(CH$_2$)$_{ab}$—O—(CH$_2$—CH$_2$O)$_{ac}$—R(72),
R(71) and R(72) are hydrogen or methyl,
u is 1 or 2,
v is zero, 1 or 2, y, z and aa are, identically or differently, zero, 1 or 2,
t is 1, 2 or 3,
R(68), R(70), R(54) and R(55) are, identically or differently, hydrogen or CH$_3$, or R(69) and R(70) and, respectively, R(54) and R(55) are, together with the carbon atom carrying them, a (C$_3$-C$_6$)-cycloalkyl;
R(63) is
H, (C$_1$-C$_4$)-alkyl, (C$_3$-C$_6$)-cycloalkyl or —C$_e$H$_{2e}$—R(73),
e is zero, 1 or 2,
R(56), R(57) and R(73) are, independently, phenyl
which is unsubstituted or is substituted by 1-2 substituents from the group F, Cl, CF$_3$, methyl, methoxy or NR(74)R(75), with R(74) and R(75) being H or CH$_3$, or R(56), R(57) and R(73) are, independently, (C$_1$-C$_9$)-heteroaryl, selected from the group consisting of pyrrolyl, imidazolyl, pyrazolyl and pyridyl,
which is unsubstituted or is substituted with phenyl;
R(58), R(59), R(60), R(61) and R(62) are hydrogen or methyl, or R(4) is R(76)—NH—SO$_2$—,
R(76) is R(77)R(78)N—(C=Y')—,
Y' is oxygen, S or N—R(79),
R(77) and R(78) are, identically or differently,
H, (C$_1$-C$_4$)-alkyl, (C$_3$-C$_4$)-alkenyl or —C$_f$H$_{2f}$—R(80),
f is zero or 1,
R(80) is (C$_5$-C$_7$)-cycloalkyl, or phenyl
which is unsubstituted or is substituted by 1-2 substituents from the group F, Cl, CF$_3$, methoxy or CH$_3$, or
R(77) and R(78) together form 4 or 5 methylene groups, of which one CH$_2$ group can be replaced by oxygen, S, NH, N—CH$_3$ or N-benzyl, where R(79) is defined as R(77), or R(4) is NR(84)R(85),
R(84) and R(85) are, independently of each other, H or (C$_1$-C$_4$)-alkyl, or together form 4 or 5 methylene groups, of which one CH$_2$ group can be replaced by oxygen, S, NH, N—CH$_3$ or N-benzyl, or of which one or two CH$_2$ groups can be replaced by CH—CH$_3$.

3. A heteroaroylguanidine I as claimed in claim 1, wherein:
R(1) is

—CO—N=C(NH$_2$)$_2$

HA is
S, and the radicals R(2) to R(4) are combined as follows:

| R(2) | R(3) | R(4) |
|---|---|---|
| H | n-BuNH— | Cl |
| H | H₂NSO₂— | PhS— |
| H | MeSO₂ | PhS— |
| H | pyrrolidin-N— | Me |
| H | pyrrolidin-N— | PhO— |
| H | piperidin-N— | Me |
| H | piperidin-N— | Cl |
| H | piperidin-N— | MeSO₂— |
| H | MeSO₂ | NH₂ |
| H | MeSO₂— | cyclopentyl-NH— |
| H | MeSO₂— | PhO— |
| H | MeSO₂— | (2-Cl-C₆H₄)S— |
| H | MeSO₂— | (4-MeO-C₆H₄)NH— |
| H | MeSO₂— | (3-Me-C₆H₄)NH— |
| H | MeSO₂— | (2,3-Me₂-C₆H₃)NH— |

-continued

| R(2) | R(3) | R(4) |
|---|---|---|
| H | Cl— | piperidin-N— |
| H | MeSO₂— | (CH₃)₂—CHCH₂—O— |
| H | MeSO₂— | (2-OMe-C₆H₄)S— |
| H | MeSO₂— | (2-Me-C₆H₄)S— |
| H | MeSO₂— | (2,5-Me₂-C₆H₃)S— |
| H | pyrrolidin-N— | (2-Cl-6-MeO-C₆H₃)— |
| H | pyrrolidin-N— | (2,3-Cl₂-6-MeO-C₆H₂)— |
| H | pyrrolidin-N— | (2-CH₃-6-MeO-C₆H₃)— |
| H | pyrrolidin-N— | (2-Cl-4-MeO-C₆H₃)— |
| H | pyrrolidin-N— | (2-OMe-6-MeO-C₆H₃)— |
| H | pyrrolidin-N— | (3-pyridyl-6-O—) |
| H | MeSO₂— | (2,6-Cl₂-C₆H₃)S— |
| H | MeSO₂— | (2,5-Cl₂-C₆H₃)S— |
| Me | Me | H |
| H | MeSO₂— | i-Pr |
| H | CF₃ | H |
| H | pyrrol-N— | Cl |

-continued

| R(2) | R(3) | R(4) |
|---|---|---|
| H | MeSO$_2$— | MeNH— |
| H | MeSO$_2$— | Et$_2$N— |
| H | t-Bu | OH |
| H | MeSO$_2$— | 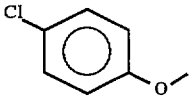 |
| H | MeSO$_2$— | 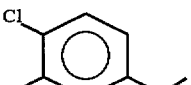 |
| H | MeSO$_2$— | 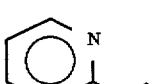 |
| H | MeSO$_2$— | 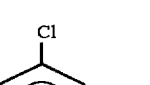 |
| H | MeSO$_2$— | 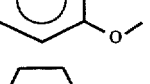 |
| H | MeSO$_2$— | 2-Naphthyl |
| H | MeSO$_2$— | 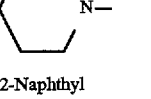 |
| H | 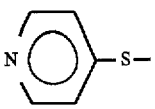 | Me |
| H | 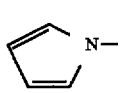 | 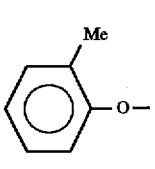 |
| H | Cl | Et$_2$N— |
| H | Me$_2$N— | H |
| H | MeSO$_2$— | 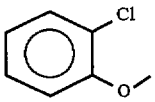 |
| H | Br | NH$_2$ |
| H | Cl | H |
| H | MeSO$_2$— | 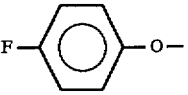 |
| H | MeSO$_2$— | 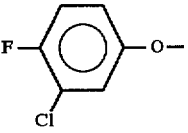 |
| H | CF$_3$ | CF$_3$ |
| H | Me | Me |

-continued

| R(2) | R(3) | R(4) |
|---|---|---|
| H | I | CF$_3$ |
| H | Me | H |
| H | H | t-Bu |
| H | MeSO$_2$— | 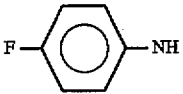 |
| H | Me | Cl |
| H | Br | Me |
| H | Cl | MeO— |
| H | MeCO— | 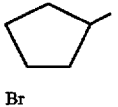 |
| H | Br | Br |
| H | MeSO$_2$— | 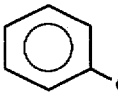 |
| H | MeSO$_2$— | 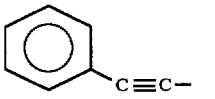 |
| NH$_2$ | Br | Me |
| H | Me$_2$N— | t-Bu |
| H | MeSO$_2$— |  |
| H |  | H |
| H | 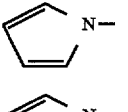 | MeO— |
| H | Me | Br |
| H | Cl | F |
| H | t-Bu | H |
| NH$_2$ | Cl | H |
| H | 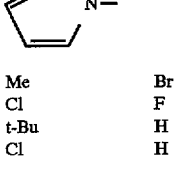 | Me$_2$N |
| H | Me$_2$N | Cl |
| H | MeSO$_2$— | 7-Isoquinolinoxy |
| H | MeSO$_2$— | 6-quinolinoxy |
| H | MeSO$_2$— | 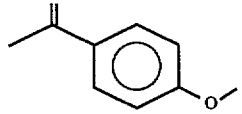 |
| H | MeSO$_2$— | 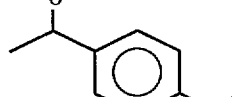 |
| H | MeSO$_2$— | (CH$_3$)$_2$CH—CH$_2$— |

| R(2) | R(3) | R(4) |
|------|------|------|
| H | MeSO₂— | cyclopentyl-methyl |
| H | Me₂N— | phenoxy |
| H | Me₂N— | 4-chloro-phenoxy |
| H | Me | Me₂N— |
| H | pyrrol-1-yl | phenoxy |
| H | Me | pyrrol-1-yl |
| H | Cl | i-Pr |
| H | pyrrol-1-yl | i-Pr |
| H | MeSO₂— | 5-quinolinoxy |
| H | cyclopentyl | CF₃ |
| H | i-Pr | MeSO₂— |
| H | i-Pr | CF₃ |
| H | H | i-Pr |
| NH₂ | Br | Br |
| H | MeSO₂— | 1-(4-methoxyphenyl)-1,2-dihydroxypropyl |
| H | pyrrol-1-yl | MeSO₂— |
| H | MeSO₂— | 2-(4-methoxyphenyl)-1-benzyl-imidazol-yl |
| H | Cl | phenylureido |
| H | Me₂N | i-Pr |
| H | MeHN— | i-Pr |
| H | Cl | Cl |
| H | Me | H₂N— |
| H | Cl | H₂N |
| H | MeSO₂— | 2-(4-methoxyphenyl)-1H-imidazol-yl |

| R(2) | R(3) | R(4) |
|------|------|------|
| H | MeSO₂— | 2,6-dimethylpiperidin-1-yl |
| H | Me₂N— | i-Pr |
| CF₃ | H | CF₃ |
| H | Br | Me |
| H | Me | Cl |
| H | Me₂N | Me |
| H | CF₃ | MeHN— |
| H | CH₃CO— | (CH₃)₂CH—CH₂ |
| H | MeSO₂— | 2-(4-methoxyphenyl)pyridin-yl |
| H | CF₃—O— | H |
| H | Me | Me₂N |
| H | Cl | Me₂N— |
| H | MeSO₂— | 5-chloro-2-[(dimethylamino)methyl]phenoxy |
| H | CH₃CO— | i-Pr |
| H | Br | BnO— |
| H | CF₃ | Br |
| H | i-Pr | MeO— |
| H | MeSO₂— | 4-(4-methoxyphenyl)pyridin-yl |
| H | MeSO₂— | 2-(4-methoxyphenyl)pyridin-yl |
| H | MeO— | t-Bu |
| H | Br | i-Pr |
| CF₃ | H | H |
| H | CF₃ | F |
| H | Ph | CF₃ |
| H | CF₃ | 1-Imidazolyl |
| H | MeCO— | t-Butylmethyl |
| H | Br | F |
| H | Br | MeO— |
| H | CF₃ | PhO— |
| H | CF₃ | Cyclopentyl |
| H | MeSO₂— | Cyclobutyl |
| H | Me | CF₃ |
| H | MeSO₂— | 4-(trifluoromethyl)-4-methoxyphenyl |
| H | OH | t-Butyl |
| H | Cl | OMe |
| H | CF₃ | i-Pr |
| F | CF₃ | H |
| F | H | CF₃ |
| H | t-Butyl | OMe |

-continued

| R(2) | R(3) | R(4) |
|---|---|---|
| H | MeCO— | 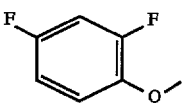 |
| H | MeCO— | 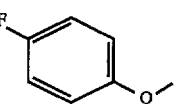 |
| H | t-Butyl | i-Butyl |
| H | CF$_3$CF$_2$— | i-Propyl |
| H | CF$_3$—SO$_2$— | 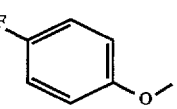 |
| Cl | CF$_3$ | H |
| Cl | H | CF$_3$ |
| H | H | Perfluoro-i-propyl |
| H | H | H |
| H | MeSO$_2$ | 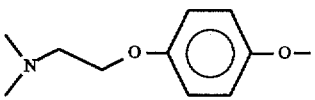 |
| H | H | Perfluoro-n-propyl |
| H | CF$_3$ | 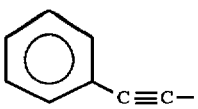 |
| H | CF$_3$ | 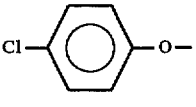 |
| H | CF$_3$ | 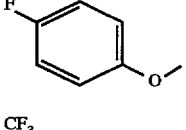 |
| H | F | CF$_3$ |
| H | MeSO$_2$— | 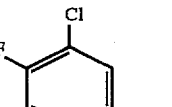 |
| H | t-Butyl | i-Propyl |
| H | t-Butyl | n-Butyl |
| H | i-Propyl | F |
| H | i-Butyl | F |
| H | Cl | 1-Imidazolyl |
| H | H | CF$_3$—CF$_2$— |
| H | H | CF$_3$ |
| H | H | 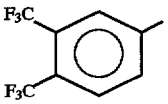 |

-continued

| R(2) | R(3) | R(4) |
|---|---|---|
| H | MeSO$_2$ | 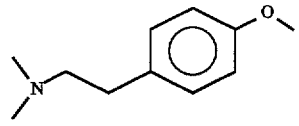 |
| H | CF$_3$SO$_2$ | i-Propyl |

4. A process for preparing a compound I as claimed in claim 1, wherein
a compound of the formula II

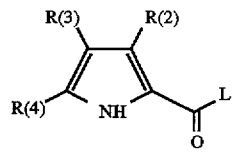

in which L is a leaving group which can readily be substituted nucleophilically, is reacted with guanidine.

5. A pharmaceutical composition for treating arrhythmias, which comprises an effective amount for said treatment of a compound of formula I as claimed in claim 1 together with a pharmaceutically acceptable carrier.

6. A method for treating arrhythmias, which comprises administering to a host in need of said treatment an effective amount of a compound of the formula I as claimed in claim 1.

7. A method for treating or prophylaxing cardiac infarct, which comprises administering to a host in need of said treatment an effective amount of a compound of the formula I as claimed in claim 1.

8. A method for treating or prophylaxing angina pectoris, which comprises administering to a host in need of said treatment an effective amount of a compound of the formula I as claimed in claim 1.

9. A method for treating or prophylaxing ischemic head conditions, which comprises administering to a host in need of said treatment an effective amount of a compound of the formula I as claimed in claim 1.

10. A method for treating or prophylaxing ischemic conditions of the peripheral and central nervous systems and of stroke, which comprises administering to a host in need of said treatment an effective amount of a compound of the formula I as claimed in claim 1.

11. A method for treating or prophylaxing ischemic conditions of the peripheral organs and limbs, which comprises administering to a host in need of said treatment an effective amount of a compound of the formula I as claimed in claim 1.

12. A method for treating shock conditions, which comprises administering to a host in need of said treatment an effective amount of a compound of the formula I as claimed in claim 1.

13. A method for protective treatment in surgical operations and organ transplantations, which comprises administering to a host in need of said treatment an effective amount of a compound of the formula I as claimed in claim 1.

14. A method for treating diseases in which cell proliferation is a primary or secondary cause, which comprises administering to a host in need of said treatment an effective amount of a compound of the formula I as claimed in claim 1.

15. A method as claimed in claim 14, wherein the disease is atherosclerosis, a late complication of diabetes, a cancer, a fibrotic disorder or prostate hyperplasia.

16. A method as claimed in claim 15, wherein the fibrotic disorder is pulmonary fibrosis, fibrosis of the liver or fibrosis of the kidneys.

17. A pharmaceutical composition for treating cardiac infarct, angina pectoris, ischemic conditions of the heart, of the peripheral and central nervous systems, of the peripheral organs and limbs, of stroke and of conditions of shock, which comprises an effective amount for said treatment of a compound of formula I as claimed in claim 1 together with a pharmaceutically acceptable carrier.

* * * * *